(12) United States Patent
Wernick et al.

(10) Patent No.: US 6,947,521 B2
(45) Date of Patent: Sep. 20, 2005

(54) IMAGING METHOD BASED ON ATTENUATION, REFRACTION AND ULTRA-SMALL-ANGLE-SCATTERING OF X-RAYS

(75) Inventors: Miles N. Wernick, Chicago, IL (US); Leroy Dean Chapman, Bolingbrook, IL (US); Oral Oltulu, Chicago, IL (US); Zhong Zhong, Stony Brook, NY (US)

(73) Assignee: Illinois Institute of Technology, Chicago, IL (US)

( * ) Notice: Subject to any disclaimer, the term of this patent is extended or adjusted under 35 U.S.C. 154(b) by 7 days.

(21) Appl. No.: 10/463,827

(22) Filed: Jun. 17, 2003

(65) Prior Publication Data

US 2004/0258202 A1 Dec. 23, 2004

(51) Int. Cl.⁷ .......................... G01N 23/04; G01N 23/20
(52) U.S. Cl. .............................. 378/70; 378/62; 378/71; 378/82; 378/86; 378/87
(58) Field of Search .............................. 378/62, 70, 71, 378/82, 83, 84, 85, 86, 87, 88, 89, 90

(56) References Cited

U.S. PATENT DOCUMENTS

| | | | |
|---|---|---|---|
| 3,628,040 A | 12/1971 | Schnopper et al. | 378/85 |
| 5,195,115 A | 3/1993 | Schiller et al. | 378/73 |
| 5,245,648 A | 9/1993 | Kinney et al. | 378/43 |
| 5,259,013 A | 11/1993 | Kuriyama et al. | 378/43 |
| 5,319,694 A | 6/1994 | Ingal et al. | 378/84 |
| 5,406,609 A | 4/1995 | Arai et al. | 378/73 |
| 5,457,726 A | 10/1995 | Miyazaki | 378/45 |
| 5,457,727 A | 10/1995 | Frijlink | 378/73 |
| 5,579,363 A | 11/1996 | Ingal et al. | 378/84 |
| 5,715,291 A | 2/1998 | Momose | 378/84 |
| 5,717,733 A | 2/1998 | Kurbatov et al. | 378/71 |
| 5,787,146 A | 7/1998 | Giebeler | 378/82 |
| 5,802,137 A | 9/1998 | Wilkins | 378/85 |
| 5,850,425 A | 12/1998 | Wilkins | 378/85 |
| 5,923,720 A | 7/1999 | Barton et al. | 378/84 |
| 5,949,847 A | 9/1999 | Terada et al. | 378/90 |
| 5,987,095 A | 11/1999 | Chapman et al. | 378/70 |
| 6,269,144 B1 | 7/2001 | Dube et al. | 378/71 |
| 6,385,289 B1 * | 5/2002 | Kikuchi | 378/79 |
| 6,577,708 B2 * | 6/2003 | Chapman et al. | 378/82 |
| 6,804,324 B2 * | 10/2004 | Martynov et al. | 378/36 |
| 2002/0136352 A1 * | 9/2002 | Protopopov | 378/36 |
| 2004/0196957 A1 * | 10/2004 | Ando | 378/82 |

OTHER PUBLICATIONS

Kenneth Lange et al.: *EM Reconstruction Alogorithms for Emission and Transmission Tomography*, Journal of Computer Assisted Tomography, pp. 306–316, 1984.

A.P. Dempster et al.: *Maximum Likelihood from Incomplete Data via the EM Algorithm*, pp. 1–38, 1976.

Hasnah et al.: *Diffraction Enhanced Imaging Constrast Mechanisms in Breast Cancer Specimens*, Medical Physics 29, pp. 2216–2221, 2002.

* cited by examiner

*Primary Examiner*—Allen C. Ho
(74) *Attorney, Agent, or Firm*—Pauley Petersen & Erickson (57) ABSTRACT

A method for detecting an image of an object by measuring the intensity at a plurality of positions of a transmitted beam of x-ray radiation emitted from the object as a function of angle within the transmitted beam. The intensity measurements of the transmitted beam are obtained by a crystal analyzer positioned at a plurality of angular positions. The plurality of intensity measurements are used to determine the angular intensity spectrum of the transmitted beam. One or more parameters, such as an attenuation property, a refraction property and a scatter property, can be obtained from the angular intensity spectrum and used to display an image of the object.

22 Claims, 5 Drawing Sheets

IMAGING METHOD BASED ON ATTENUATION, REFRACTION AND ULTRA-SMALL-ANGLE-SCATTERING OF X-RAYS

This work was supported in part by U.S. Army Grant DAMD 17-99-1-927; U.S. Department of Energy Contract DE-AC02-76CH00016; State of Illinois Higher Education Cooperative Agreement; and National Institutes of Health Grants GM59395 and AR48292.

FIELD OF THE INVENTION

This invention relates to a method for detecting an image of an object, such as one mass internal with respect to another mass. The method of this invention measures the intensity of an x-ray beam as it emits from an object as a function of angle. An angular intensity spectrum of the emitted beam is determined and is used to infer parameters which describe, for example, the scatter, refraction and/or attenuation properties of the object.

BACKGROUND OF THE INVENTION

X-ray imaging has been used in the medical field and for radiology in general, such as non-destructive testing and x-ray computed tomography. Conventional radiology systems use x-ray absorption to distinguish differences between different materials, such as normal and abnormal human tissues.

Conventional x-ray imaging techniques, such as used in mammography, typically use a flood of x-rays to illuminate an object. A detection system, such as including a phosphor screen and a photographic film, is used to measure only the attenuation properties of the object by measuring the intensity of the x-rays that emerge from the object.

X-ray imaging for screening mammography has been used to identify early stages of breast cancer. It is well known that breast cancer mortality among women under screened controls can be significantly reduced when compared with unscreened controls. Mammography tends to identify smaller and less advanced stages of cancer, when compared with cancers found by breast physical examination or breast self-examination. Treatment of smaller and less advanced stages of breast cancer result in better survival rates. It is quite apparent that enhanced radiology methods can be used to detect even smaller and earlier stage breast cancers. Approximately 10% of clinically obvious breast cancers are not visible in images produced by conventional mammography methods. In addition, it is typically difficult to distinguish between benign lesions and malignant ones using conventional radiology.

In particular, breast cancer which is not visible with conventional mammography methods occurs most frequently in patients with relatively large amounts of breast glandular tissue. The density of the breast glandular tissue tends to obscure underlying pathology. In order to detect early stages of cancer, it is desirable to increase the sensitivity of mammography so that smaller and earlier stages of breast cancer can be detected. Earlier detection of breast cancer may result in significantly reduced mortality rates.

Mammographic technology has improved dramatically over the last two decades. For example, dedicated mammography equipment now exists with appropriate x-ray beam quality, adequate breast compression and automatic exposure control. However, conventional mammographic technology still depends upon the depiction of x-ray absorption to define differences between normal and abnormal tissues.

Limitations of conventional radiology are also apparent in imaging cartilage, such as during detection and treatment of injuries or degenerative joint diseases, such as osteoarthritis. Better imaging techniques would be beneficial for detecting such degenerative diseases earlier, such as before the point of irreversible damage.

Ingal et al., U.S. Pat. No. 5,319,694 discloses a method for obtaining an image of an internal structure of an object. Radiation transmitted through an object is collimated by a Laue type crystal analyzer. While deflecting the crystal analyzer, interferogram images of the internal structure of the object are monitored and a position of the crystal analyzer which provides an image with maximum contrast is selected. Both the transmitted beam and the diffracted beam emerging from the crystal analyzer carries information on the internal structure of the object. Simultaneous observation of the object in both the transmitted beam and the diffracted beam allows detection of artifacts in the image. Once the image is detected, the crystal analyzer is set to a position at which the maximum contrast of the object image is attained.

According to U.S. Pat. No. 5,319,694, simultaneous registering of images in a transmitted beam and a diffracted beam enables definition of minor and low-contrast image elements and elimination of errors in interpretation of the image due to the imperfection of the image detector. Algebraic addition of the transmitted image and the diffracted image enhances the contrast of the boundaries between different-density media, which is due to elimination of background resulting from photoelectric absorption of radiation in the object. A detector that detects the diffracted beam has a feedback loop output which is connected to a precision displacement actuator which moves the crystal analyzer.

There is an apparent need for mammographic and radiologic methods that can be used to detect even smaller and earlier stages of breast cancer, than the stages of breast cancer that can be detected with conventional imaging technology.

There is a need for improved radiologic methods that can be used to detect small changes in joint tissues, such as cartilage. There is also a need for a radiologic imaging method that can characterize materials, such as tissue, for research and treatment of diseases.

There is a need for an x-ray imaging method that provides clearer images on a pixel-by-pixel basis of an object. There is a need for an imaging method that provides images based upon x-ray properties other than absorption, such as refraction and scatter.

SUMMARY OF THE INVENTION

It is one object of this invention to provide a method for detecting an image of an object and using the image to determine differences in composition of matter and/or structural arrangement of the object.

It is another object of this invention to provide a method for detecting an image using one or more of several parameters determined from the intensity of an x-ray beam transmitted through an object as a function of angle.

It is yet another object of this invention to provide a method for producing image values that can be used to characterize materials, such as tissues by statistical pattern recognition.

The above and other objects of this invention are accomplished with a method that irradiates an x-ray beam, such as a conventional x-ray beam or a mono-energetic synchrotron beam, through an object and directs a transmitted beam, which is emitted from the object, at an analyzer, preferably a crystal analyzer such as a Bragg type crystal analyzer or a Laue type crystal analyzer. The analyzer is positioned at a plurality of angular positions to measure the intensity of the transmitted beam at each of the angular positions. At least one parameter, such as an attenuation property, a refraction property and a scatter property, of the object is obtained from the intensity measurements. One or more of the parameters is used to display an image of the object. In one embodiment, an estimated angular intensity spectrum of the transmitted beam can be determined as a function of a sensitivity of the analyzer. The at least one parameter of the object can be obtained from the estimated angular intensity spectrum. The method of this invention results in significantly enhanced clarity of the image of the object and depicts informative object properties not depicted by other imaging methods.

The imaging method of this invention can be referred to as Multiple Image Radiography (MIR), as it can use the angular intensity spectrum of the transmitted x-ray beam to display multiple images based on parameters, alone or in combination, such as the attenuation, refraction and/or scatter properties. The method of this invention is particularly useful for materials exhibiting low absorption contrast, which are not visualized well using conventional radiography, such as breast glandular tissue and joint connective tissues. The MIR method according to this invention uses x-ray sources, such as, for example, conventional x-ray sources or relatively high intensity synchrotron radiation, to create a mono-energetic pixel scan imaging system. By transmitting the x-ray beam through the object, the estimated angular intensity spectrum can be used to display an image of the object on a pixel-by-pixel basis.

By placing the analyzer in a plurality of angular positions with respect to the transmitted beam, a plurality of intensity measurements are obtained from the transmitted beam. The intensity measurements can be described mathematically in terms of a convolution integral between the true angular intensity spectrum of the x-rays within the transmitted beam and the sensitivity of the analyzer as a function of angle, i.e., the intrinsic rocking curve of the analyzer. Using a deconvolution operation to invert the convolution integral, the estimated angular intensity spectrum of the transmitted beam is inferred at each measured pixel of the object. The estimated angular intensity spectrum is then used to obtain at least one parameter that can be used to display the image of the object.

Alternatively, the at least one parameter can be computed directly from the measured angular intensity spectrum data through the use of a mathematical model based on a convolutional or similar assumption. In yet another alternative embodiment, a parameter describing ultra-small-angle scatter can be computed by subtracting an attenuation image from an image acquired at a peak of the analyzer rocking curve.

BRIEF DESCRIPTION OF THE DRAWINGS

The above-mentioned and other features and objects of the invention will be better understood from the following detailed description taken in conjunction with the drawings.

DETAILED DESCRIPTION OF THE PRESENTLY PREFERRED EMBODIMENTS

The method of this invention can provide imaging of an object on a pixel-by-pixel measurement, however, for faster data acquisition line or area scanning are preferred. At each pixel of the object, an x-ray beam is transmitted through a first view of the object. The beam emits from an opposite side of the object. The effect the object has on the beam emitted from the object, referred to herein as a transmitted beam, is dependent on the physical makeup of the object. Analysis of the transmitted beam, such as by using a system of diffracting crystals, determines the spectrum of angular x-ray components of the transmitted beam. Thus, information on the effect of the x-ray beam by the object can be obtained. This information can be used to describe physical properties of the object and to provide an image of the object.

Figure 1:
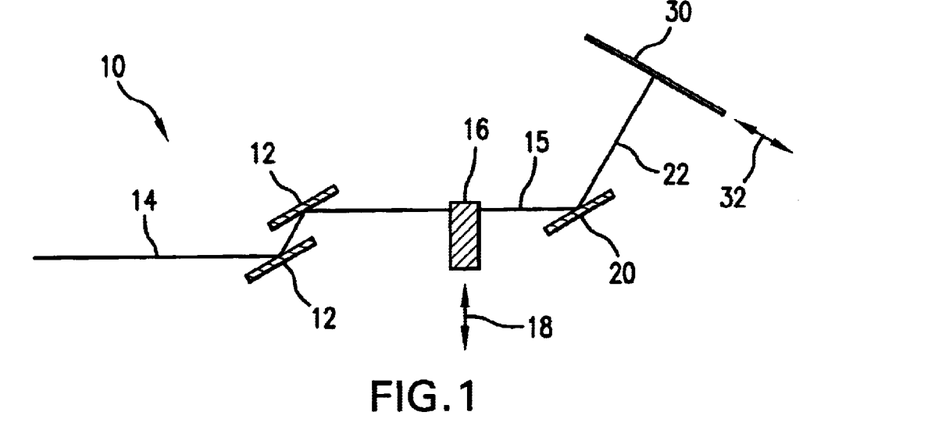
FIG. 1 is a schematic diagram of a crystal analyzer system setup according to one embodiment of this invention.

FIG. 1 shows a schematic diagram of analyzer system 10, according to one preferred embodiment of this invention. Analyzer system 10 includes double crystal monochromator 12 which can be used to monochromate and collimate x-ray beam 14. X-ray beam 14 is desirably a mono-energetic synchrotron beam. Each crystal of monochromator 12 is preferably constructed of silicon using a (3, 3, 3) lattice planes structure. The lattice planes used in monochromator 12, such as the (3, 3, 3) lattice planes, should preferably match those used in crystal analyzer 20. Through experimentation, the (3, 3, 3) lattice planes structure increased the sensitivity to refraction effects by a factor of about 5, when compared to experiments conducted with (1, 1, 1) lattice planes structure. According to one preferred embodiment of this invention, x-ray beam 14 has an energy level in a range of approximately 10 keV to approximately 100 keV, and desirably approximately 18 keV to approximately 40 keV, with a bandwidth of approximately 1.5 eV.

Analyzer system 10 can be used to produce an image of object 16. At least one x-ray beam 14 is transmitted through a first view of object 16. The x-ray beam is transmitted through the object 16. The intensity of x-ray beam 14 is affected by object 16, and transmitted beam 15 is emitted from object 16. The characteristics of transmitted beam 15 are dependent on the physical properties of object 16. Transmitted beam 15 is directed at analyzer 20. Analyzer 20 measures the intensity within transmitted beam 15 with a detector by generating diffracted beam 22. Detector 30 shown in FIG. 1, which can be a digital detector or an image plate, measures the intensity of the selected small range of angles from transmitted beam 15 which are directed to detector 30 by analyzer 20.

In one embodiment of this invention the analyzer 20 measures the intensity in the ultra-small-angle scatter regime, referring to the small range of divergence angles of transmitted beam 15 which are diffracted by analyzer 20. The images obtained by the method of this invention differ from the images obtained according to conventional radiography technology, which does not use a crystal analyzer, in that the image contains nearly no scatter from object 16 other than the ultra-small-angle scatter the method of the invention seeks to measure, primarily due to extremely tight conditions imposed by a Bragg type crystal scattering condition. Any rays which are deviated by even a few microradians from a direct path and/or which are deviated in energy by a few electron volts, such as $\Delta E/E \geq 10^{-4}$, will not be diffracted by analyzer 20. Such arrangement will remove relatively small angle scattering and other forms of coherent scatter, and will also remove Compton scattering. These types of scattering mechanisms contribute to loss of contrast in imaging. Thus, diffracted beam images provided by the methods of this invention are almost completely free of undesired (i.e., not measured) forms of scatter.

The method according to this invention can be conducted with either a Bragg type crystal analyzer 20 or a Laue type crystal analyzer 20. A Bragg type system uses reflection geometry to obtain refraction, attenuation and scatter images in a near absence of coherent and inelastic scattering. Reflection geometry of the Bragg type system provides a single diffracted beam image at a single setting of the crystal analyzer. An image produced with a Bragg system can provide a refraction angle image of the object, an improved, nearly scatter-free attenuation (absorption) image of the object, and a scatter image of the object. Analyzer 20, as shown in FIG. 1, represents a Bragg type crystal analyzer.

Any suitable detector known to those skilled in the art can be used to detect an image of object 16. In one preferred embodiment according to this invention, the image of object 16 is detected with a detector which comprises a photostimulable phosphor image plate typically used for radiology, such as FUJI Medical Systems high resolution HR5 and standard resolution ST5 image plates. An image recorded on detector 30 can be digitized, stored and displayed, for example by a FUJI Medical Systems AC3 reader and workstation or by any other suitable digital conversion means known to those skilled in the art. A suitable spatial resolution of images can be 50 microns by 50 microns.

According to one preferred embodiment of this invention, object 16 is moved in a direction relative to x-ray beam 14, shown in FIG. 1 by arrow 18. Detector 30, or another suitable detector, moves in a direction perpendicular to diffracted beam 22, as shown in FIG. 1 by arrow 32, and relative to the movement of object 16 so as to detect diffracted beam 22 from analyzer 20. Such scanning can be accomplished, for example by a computer controlled stepper motor translation stage which holds a support for object 16.

Analyzer 20 is preferably positioned between object 16 and detector 30, is preferably fixed spatially with respect to transmitted beam 15 and oriented to diffract transmitted beam 15 onto detector 30. Analyzer 20 can be positioned at a plurality of angular positions for measuring the intensity of transmitted beam 15 at each of the angular positions. Fine angular control of analyzer 20 can be accomplished with a stepper motor driven translation stage pushing on a relatively long rod which is mechanically connected to an axle onto which crystal analyzer 20 is attached. The fine angular control may result in a resolution limit of approximately 1.0 microradian. Such fine tuning can position crystal analyzer 20 at various positions within a rocking curve of x-ray beam 14.

Figure 2:
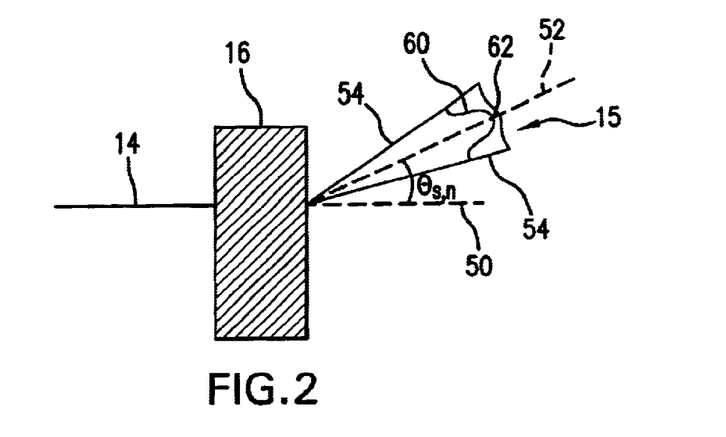
FIG. 2 is an enlarged view of a portion of the schematic shown in FIG. 1.

FIG. 2 shows a greatly exaggerated view of x-ray beam 14 transmitting through object 16 and transmitting beam 15 emitting from an opposite side of object 16. FIG. 2 shows the divergence and refraction of transmitted beam 15 from the original path of x-ray beam 14, although for illustrative purposes, the angular spread of divergence and the angle of refraction for transmitted beam 15 are greatly exaggerated. For example, the divergence of transmitted beam 15 is typically on the order of nanoradians or microradians.

Divergence is due to x-ray beam 14 passing through object 16 and the physical properties of object 16. The divergence or refraction angles of each x-ray component of transmitted beam 15 can be determined by measuring the angle between the original path of x-ray beam 14 and the path of the diverging x-ray component present in transmitted beam 15. For example, in FIG. 2, dotted line 50 represents an extension of the original path of x-ray beam 14 and the refraction angle of dotted line 52, which extends through the centroid of transmitted beam 15, from dotted line 50 is angle $\theta_{s,n}$.

Positioning analyzer 20 at a plurality of angular positions relative to transmitted beam 15 allows for the measurement of the intensity at various points of transmitted beam 15. The intensity measurements can be used to determine the angular intensity spectrum within the transmitted beam 15. The angular intensity spectrum of transmitted beam 15 is illustrated generally in FIG. 2 as representative curve 60. Curve 60 includes peak 62 which represents the point of greatest x-ray intensity. In FIG. 2, peak 62 corresponds to dotted line 52 which extends through the centroid (the midpoint) of transmitted beam 15. Transmitted beam 15 decreases in intensity, as shown by curve 62, toward the two radial edges 54 of transmitted beam 15.

The true angular intensity spectrum, or true angular intensity distribution, of transmitted beam 15 is defined as the intensity within transmitted beam 15 as a function of angle. The true angular intensity spectrum of transmitted beam 15 can be determined by measuring the intensity of the transmitted beam 15 at more than two angular positions, determining a measured angular intensity spectrum, and taking into account the sensitivity of the analyzer system 10, i.e., subtracting out the intrinsic rocking curve of the analyzer system 10. The sensitivity function of analyzer system 10, known as the intrinsic rocking curve of analyzer system 10, characterizes the x-ray output as a function of the angular position of analyzer system 10 when no object is present in x-ray beam 14, as prepared by the monochromator 12.

The intensity measurements, or measured angular intensity spectrum, obtained by the analyzer system 10 can be described mathematically in terms of a convolution integral between the desired true angular intensity spectrum of transmitted beam 15 and the intrinsic rocking curve of analyzer system 10. In the absence of noise, the intensity (y) of the transmitted beam 15 measured at pixel n (n=1, ..., N) after reflecting from analyzer 20 can be modeled as:

$$y_n(\theta) = R(\theta) * f_n(\theta), \quad (1)$$

where * denotes convolution, $R(\theta)$ is the sensitivity function, or intrinsic rocking curve, of analyzer system 10, and $f_n(\theta)$ is the true angular intensity spectrum of transmitted beam 15. The intensity data of the disclosed method are obtained at a plurality of discrete angular positions of the analyzer $\theta_k$(k=1, ..., K). Therefore, in the absence of noise, the observed data can be modeled as:

$$y_n[k] = [R(\theta) * f_n(\theta)]_{\theta=\theta_k}, \quad (2)$$

One skilled in the art guided by the teachings herein will appreciate that many more-detailed models of the system output can be contemplated, however this simple model captures the essential characteristics of the observations.

Using a synchrotron as a source of x-ray beam 14 provides a relatively low noise level. However, employing a more conventional x-ray source may be photon-limited, and thus produce noise that is Poisson-distributed. For computation purposes, a discrete model of the data including the effect of noise can be written as:

$$y_n[k] \sim \text{Poisson}(R[k] * f_n[k]), \quad (3)$$

where $y_n[k]$, $R[k]$ and $f_n[k]$, k=1, ..., K, are discrete representations of $y_n(\theta)$, $R(\theta)$ and $f_n(\theta)$, respectively.

In one embodiment, the method of this invention includes estimating the angular intensity spectrum of transmitted beam 15, which results from x-ray beam 14 passing through object 16 for each pixel of detector 30. This pixel-by-pixel measurement of object 16 provides a thorough representation of the effect of object 16 on x-ray beam 14, and therefore provides information for describing the physical properties of object 16.

The estimated angular intensity spectrum of each pixel of object 16 is determined as a function of a sensitivity of analyzer system 10. As discussed above, the intensity measurements of each pixel obtained by analyzer system 10 at the angular positions can be described mathematically in terms of a convolution integral between the true angular intensity spectrum of transmitted beam 15 and the rocking curve of analyzer system 10. The estimated angular intensity spectrum, i.e., the estimate of the true angular intensity spectrum, at each pixel can then be determined using a deconvolution operation that inverts an effect of the convolution integral.

The deconvolution operation generally estimates the true angular intensity spectrum of transmitted beam 15, resulting in the estimated angular intensity spectrum. In one embodiment of this invention, the estimated angular intensity spectrum of transmitted beam 15 is determined directly by numerically computing the deconvolution operation. To compute the estimated angular intensity spectrum $\hat{f}_n[k]$ from the measured angular intensity spectrum $y_n[k]$, the observation model of Equation 3, described above, is inverted separately for each pixel. As will be appreciated by one skilled in the art, there are many ways to approach this deconvolution problem. One example of a deconvolution operation is the expectation-maximization (EM) algorithm for maximum-likelihood (ML) estimation, referred to below as the "EM algorithm," as disclosed by A. P. Dempster, N. M. Laird and D. B. Rubin in "Maximum likelihood from incomplete data via the EM algorithm," *J. Roy. Statist. Sect.*, vol. 39, pp. 1–38 (1997), herein incorporated by reference.

When applied to a Poisson linear model, such as in Equation 3, the EM algorithm yields an iteration for reconstruction of emission tomography images, as disclosed by K. Lange and R. E. Carson in "EM reconstruction algorithms for emission and transmission tomography," *J. Comput. Assist. Tomogr.*, vol. 9, pp. 306–316 (1984), herein incorporated by reference. Adapting the iteration for deconvolution of Equation 3 results in the following iterative expression:

$$f^{(i+1)}[k] = \frac{f^{(i)}[k]}{\sum_{k=1}^{K} R[k]} \left\{ R[k] \star \left[ \frac{y[k]}{R[k] * f^{(i)}[k]} \right] \right\}, \quad (4)$$

where $f_n^{(i)}[k]$ is the estimate of $\hat{f}_n[k]$ at iteration i, and $\star$ denotes cross-correlation.

By using the angular intensity spectrum of each pixel of object 16, one or more of several parameters, such as a numerical parameter representing an attenuation (absorption) property, a refraction property, and a scatter property, can be obtained at each pixel of the detector. Using the estimated angular intensity spectrum $\hat{f}_n[k]$ of each pixel, such parameters are obtained, and an image of object 16 can then be displayed using one or more of the parameters. In one embodiment of the invention, the estimated angular intensity spectrum can be summarized by parameters defined specifically to highlight image features indicative of specific diseases.

These parametric images are defined in terms of the following quantities: the total intensity at pixel n, $$T_n = \sum_{k=1}^{K} \hat{f}_n[k]; \quad (5)$$

the angular intensity spectrum at this pixel normalized by its total intensity, $$F_n[k] = \frac{\hat{f}_n[k]}{T_n}; \quad (6)$$

and the total intensity at each pixel in the absence of the object, $$I_0 = \sum_{k=1}^{K} R[k]; \quad (7)$$

where $\hat{f}_n[k]$ is the estimated value of $f_n[k]$.

In the ultra-small-angle range, attenuation of an x-ray beam can be caused by both attenuation and scatter into angles outside the measured range. The attenuation property ($a_n$) of object 16, can be represented by the following effective attenuation parameter for each pixel of object 16:

$$a_n = -\ln \frac{T_n[k]}{I_0}. \quad (8)$$

The attenuation parameter $a_n$ is proportional to the integral of the attenuation characteristic over the path of the beam.

The attenuation image provided by the method of this invention measures the same property as a conventional radiograph, however, due to a more exact imaging model and the consideration of scatter, it is generally a clearer and more detailed image than an image obtained using conventional radiography methods or other x-ray imaging systems.

Refraction results in a slight overall deflection of the x-ray beam. The refraction properties of object 16 can be represented by measuring the displacement of a centroid of the angular intensity spectrum. The displacement is caused by the presence of object 16. Refraction angle ($\theta_{s,n}$) is represented mathematically by the following:

$$\theta_{s,n} = \left( \sum_{k=1}^{K} kF_n[k] - \frac{1}{I_0} \sum_{k=1}^{K} kR[k] \right) \Delta\theta; \quad (9)$$

where $\Delta\theta$ is the angular spacing of the samples in $F_n[k]$. The refraction image provided by the method of this invention, due to a more exact imaging model and the consideration of scatter, is generally clearer and more detailed than an image obtained using conventional radiography methods or other x-ray imaging methods.

Ultra-small-angle scatter influences the shape of the angular intensity spectrum. Ultra-small-angle scatter can be quantified by viewing the angular intensity spectrum as a probability density function, and measuring its variance, kurtosis and/or skewness.

Broadening of the beam by ultra-small-angle scatter can be described by the beam's angular divergence about the refraction angle, as measured by the second central moment (variance) of the normalized angular intensity spectrum, i.e., $$s_n = \sum_{k=1}^{K} (k\Delta\theta - \theta_{s,n})^2 F_n[k]; \quad (10)$$

where $\Delta\theta$ is the angular spacing of the samples in $F_n[k]$.

The angular intensity spectrum of a pixel is broadened, and therefore less peaked, due to scatter. Kurtosis is zero for a Gaussian-shaped function, greater than zero for highly peaked (leptokurtic) functions and less than zero for flatter (platykurtic) functions. Kurtosis can be defined as the following:

$$kurt_n = \sum_{k=1}^{K} (k\Delta\theta - \mu)^4 F_n[k] - 3 \left( \sum_{k=1}^{K} (k\Delta\theta - \mu)^2 F_n[k] \right)^2, \quad (11)$$

where $\mu$ is the centroid of $F_n[k]$.

The combination of scatter and inhomogeneous refractive index can cause the estimated angular intensity spectrum to become skewed. This property can be measured by a skewness parameter of the function, defined by the following:

$$\mu_{3,n} = \sum_{k=1}^{K} (k\Delta\theta - \mu)^3 F_n[k]. \quad (12)$$

In another embodiment of this invention, the desired estimated angular intensity spectrum is determined indirectly by postulating a model of the angular spectrum a priori and estimating the parameters of the model. As will be appreciated by one skilled in the art, such a model-based approach can be implemented by several methods known in the art.

In another embodiment, an ultra-small-angle scatter image is obtained without performing a deconvolution step to determine the estimated angular intensity spectrum. Instead, for example, the variance parameter $S_n$ at pixel n can be determined directly from the measured angular intensity spectrum by using the following equation:

$$S_n = S_{M,n} - S_{R,n}; \quad (13)$$

where $S_{M,n}$ is the variance parameter at pixel n of the measured angular intensity spectrum and $S_{R,n}$ is the variance parameter at pixel n of the rocking curve. This relationship relies on the fact that the variance of the convolution of two normalized functions is equal to the sum of the variances of these two functions. As will be appreciated by one skilled in the art, other parameters of the angular intensity spectrum can be similarly determined.

In yet another embodiment of this invention, the ultra-small-angle scatter image is obtained in an approximate way by using an attenuation image and an image acquired with the analyzer positioned so that measurements are acquired at a peak of the rocking curve of the analyzer (also referred to as the "top image"). The attenuation image may be obtained in various ways, including by the diffraction-enhanced imaging method as disclosed Chapman et al. In U.S. Pat. No. 5,987,095, issued 16 Nov. 1999, herein incorporated by reference, by conventional radiography, or by using the system in FIG. 1 with analyzer 20 removed and detector 30 positioned so as to detect beam 15. The intensity of the top image can be influenced by three factors: 1) the top image can be reduced by attenuation; 2) the top image can be reduced as a result of beam broadening by scatter; and 3) the top image can be reduced due to a shift of the angular intensity spectrum by refraction. An approximate ultra-small-angle scatter image can be obtained by subtracting the attenuation image from the top image.

In general, x-ray image display is the process of representing numerical measures of a physical property in terms of image brightness and/or color. When, as in conventional x-ray imaging, only one numerical measure is obtained for each point in the image, the image can be displayed as a monochrome image or by using a pseudocolor representation in which each possible value of the numerical measure is represented as a different color. As discussed above, the method of this invention provides an estimated angular intensity spectrum curve at each pixel of object 16. The curve is then reduced to a set of parameters. Each of the parameters provided by this invention can be visualized as a monochrome or pseudocolor image. A more complex image can be displayed by visualizing multiple parameters simultaneously. For example, one parameter can be represented as monochrome intensity, while another parameter is represented as an overlaid color map. In another embodiment, each parameter can be used to display an image in a different color, such as red for attenuation, green for refraction, and blue for scatter (RGB display), and displayed together in a color composite. As will be appreciated by one skilled in the art, other methods of displaying a three-value image in color, such as HSV (hue, saturation, value) and principal component analysis can be used with the parameters obtained by the method of this invention to display a multi-color image.

Figure 3:
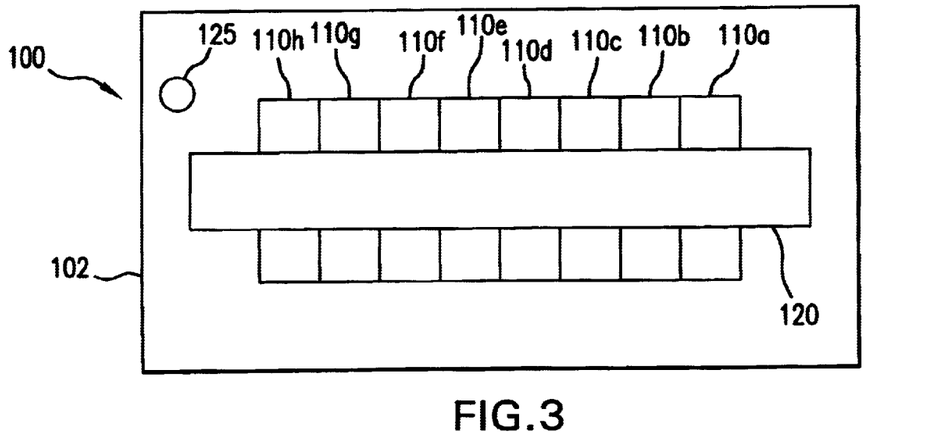
FIG. 3 is an illustration of a phantom used to produce example images according to the method of this invention.

To demonstrate imaging of an object by the parameter of the method of this invention, a physical phantom was constructed in such a way as to create various combinations of refraction, attenuation and scatter effects. FIG. 3 shows phantom 100 including Lucite™ substrate 102. Lucite™ substrate 102 had a thickness of 6.35 millimeters. Sheets of paper were positioned in a staggered arrangement on the Lucite™ substrate 102 to form paper stacks 110a–h. Paper stack 110a includes one sheet of paper, paper stack 110b includes two sheets of paper, paper stack 110c includes three sheets of paper, paper stack 110d includes four sheets of paper, paper stack 110e includes five sheets of paper, paper stack 110f includes six sheets of paper, paper stack 110g includes seven sheets of paper and paper stack 110h includes eight sheets of paper. Cylindrical Lucite™ rod 120 was placed across the paper stacks 110a–h. Lucite™ rod 120 had a radius of 6 millimeters and a length of 51 millimeters. Steel ball 125 was placed on Lucite™ substrate 102 for purposes of alignment.

Phantom 100 was placed in an analyzer system as shown in FIG. 1. The analyzer system included a crystal monochromator and a crystal analyzer, both constructed of silicon having a (3, 3, 3) lattice planes structure. The detector included an x-ray photostimulable Fuji HR-V image plate and a Fuji BAS-2500 reader having a pixel size of 50 microns×50 microns, available from Fuji Medical Systems, Stamford, Conn. The x-ray beam source was a National Synchrotron Light Source X15A, available at Brookhaven National Laboratory, Upton, N.Y.

Using an 18 keV x-ray beam, 24 images of the phantom were acquired at 0.8 microradian increments from −9.6 to +8.8 microradians. The photon flux incident on phantom 100 was approximately $5.3 \times 10^6$ photons/square millimeter (100 millirads, 1 milliGy). Each image consisted of 1256×444 pixels, each having a diameter of 50 microns×50 microns. Background and scatter radiation from the synchrotron were reduced by using filtering slits. The remaining background radiation was subtracted from every pixel in each image.

Figure 4A:
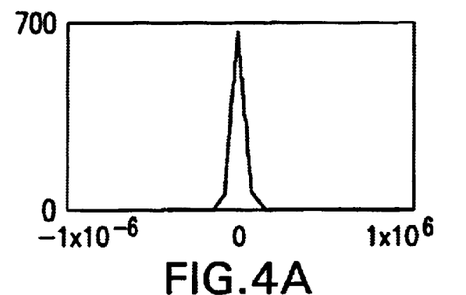
FIG. 4A is an estimated angular intensity spectrum curve of one representative pixel of the phantom illustrated in FIG. 3.
Figure 4B:
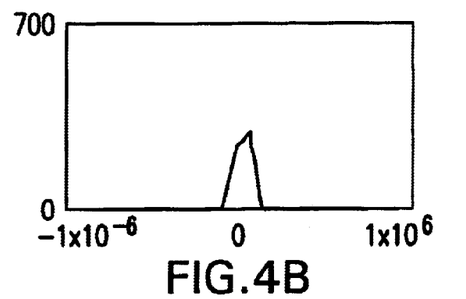
FIG. 4B is an estimated angular intensity spectrum curve of a second representative pixel of the phantom illustrated in FIG. 3.
Figure 4C:
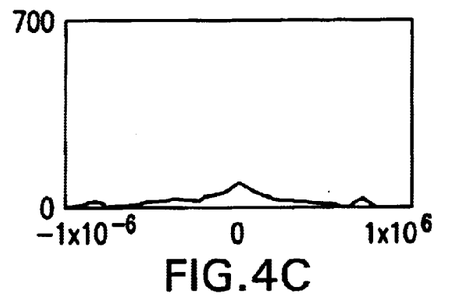
FIG. 4C is an estimated angular intensity spectrum curve of a third representative pixel of the phantom illustrated in FIG. 3.
Figure 4D:
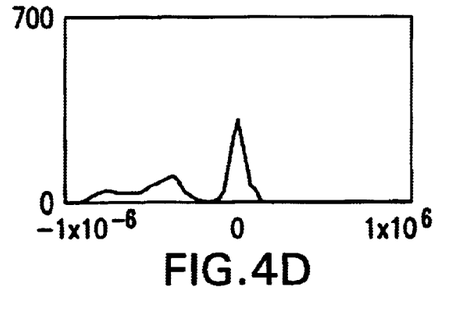
FIG. 4D is an estimated angular intensity spectrum curve of a fourth representative pixel of the phantom illustrated in FIG. 3.

The deconvolution procedure described above was used to determine the angular intensity spectrum of each pixel. FIG. 4A illustrates the estimated angular intensity spectrum $\hat{f}_n[k]$ of a representative pixel of Lucite™ substrate 102. FIG. 4B illustrates the estimated angular intensity spectrum $\hat{f}_n[k]$ of a representative pixel of Lucite™ rod 120. FIG. 4C illustrates the estimated angular intensity spectrum $\hat{f}_n[k]$ of a representative pixel of the stack of paper 110h. FIG. 4D illustrates the estimated angular intensity spectrum $\hat{f}_n[k]$ of a representative pixel of the edge of Lucite™ rod 120.

Figure 5:
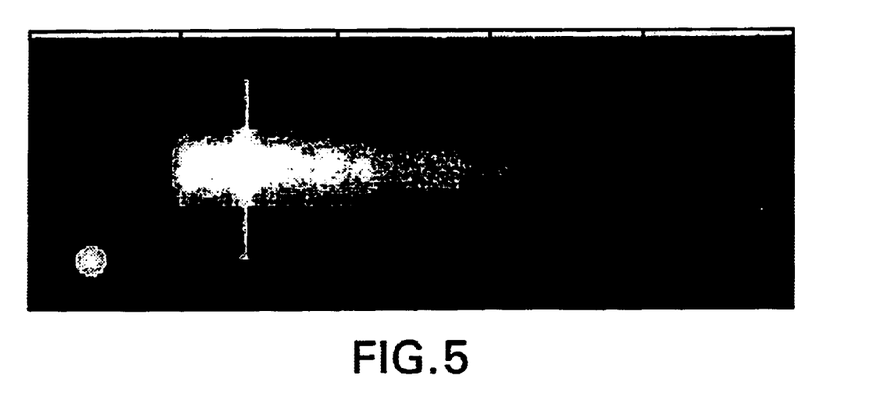
FIG. 5 is a photograph of an attenuation image of the phantom illustrated in FIG. 3 obtained by the method of this invention.
Figure 6:
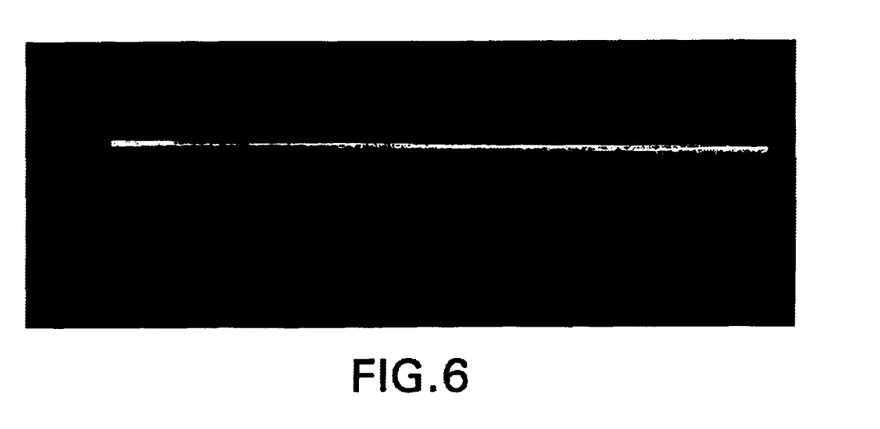
FIG. 6 is a photograph of a refraction image of the phantom illustrated in FIG. 3 obtained by the method of this invention.
Figure 7:
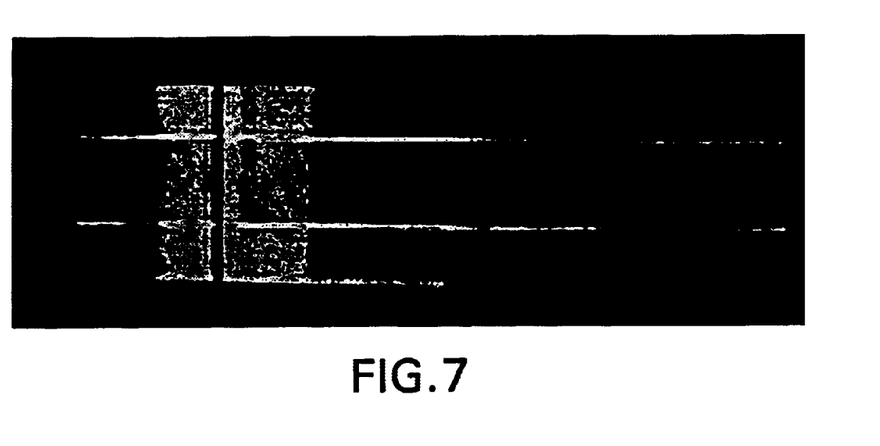
FIG. 7 is a photograph of a variance image of the phantom illustrated in FIG. 3 obtained by the method of this invention.
Figure 8:
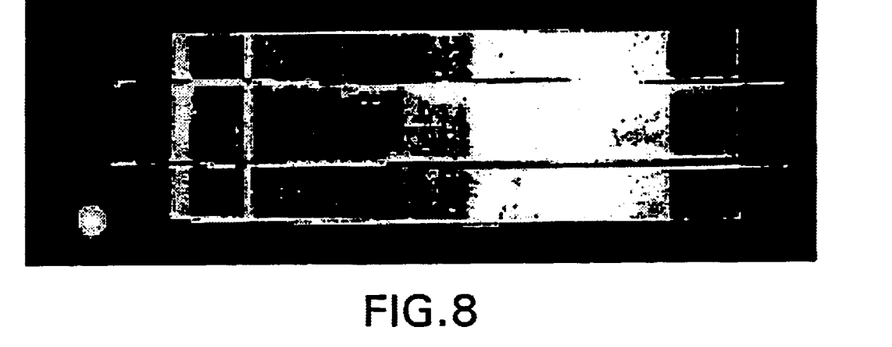
FIG. 8 is a photograph of a kurtosis image of the phantom illustrated in FIG. 3 obtained by the method of this invention.
Figure 9:
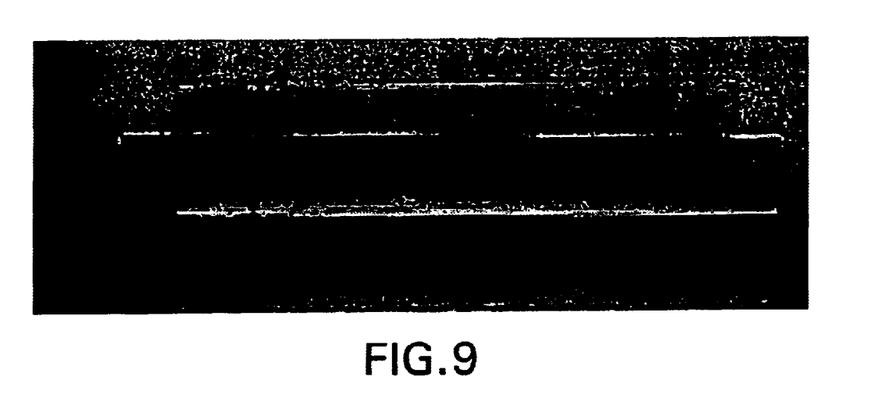
FIG. 9 is a photograph of a skewness image of the phantom illustrated in FIG. 3 obtained by the method of this invention.
Figure 10:
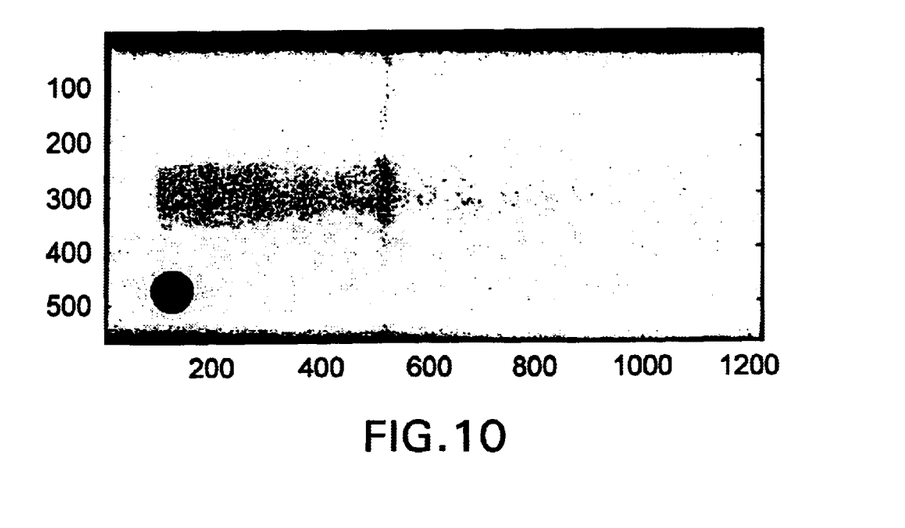
FIG. 10 is a photograph of an image of the phantom illustrated in FIG. 3 obtained by conventional radiography.

The estimated angular intensity spectra of the pixels of phantom 100 were used to determine the following pixel parameters: attenuation, refraction, variance, kurtosis and skewness of phantom 100. Each of the pixel parameters were used to generate images of phantom 100. FIG. 5 is the attenuation image of phantom 100. FIG. 6 is the refraction image of phantom 100. FIG. 7 is the variance image of phantom 100. FIG. 8 is the kurtosis image of phantom 100. FIG. 9 is the skewness image of phantom 100. FIGS. 5–9 are displayed as monochrome images, however these images could be displayed through use of color and/or by mathematical transformations. FIG. 10 is an image of phantom 100 obtained by conventional radiography, i.e., without a crystal analyzer, for comparison. The image of FIG. 10 was obtained using the same system as in FIGS. 5–9, except the detector was placed in front of the analyzer.

Figure 11:
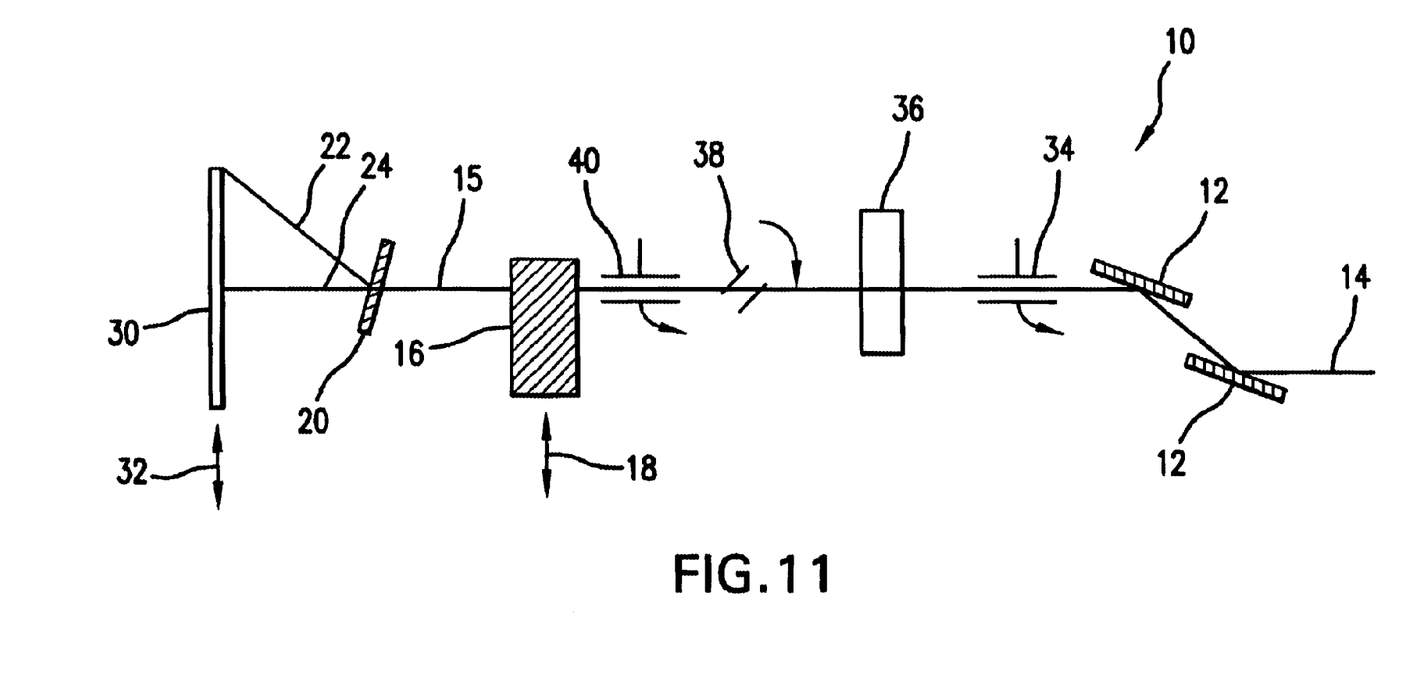
FIG. 11 is a schematic diagram of a crystal analyzer system setup according to another embodiment of this invention.

When using a Laue crystal analyzer system 10, as shown in FIG. 11, transmission geometry is used to obtain images in the same manner as with a Bragg system. However, the Laue system has two main differences over the Bragg system. First, in a Laue system forward diffracted beam 24 is emitted from crystal analyzer 20 in addition to diffracted beam 22. Diffracted beam 22 produces an image which contains some of the scatter rejected by the diffracted beam image. Information contained within the diffracted beam image can be used to detect and image scatter resulting from transmitted beam 15 passing through object 16. Second, the intensity of the image downstream of crystal analyzer 20 in a Laue system is not as intensity efficient as in a Bragg system. When analyzer 20 has an optimal crystal thickness, diffracted beam 22 is approximately 10% of the beam intensity that it is when striking an entrance side of crystal analyzer 20. The efficiency of a Bragg system is approximately 50% or greater than the entrance beam intensity.

Diffracted beams 22 will also be detected at each of the plurality of the angular positions of analyzer 20. From such information, refraction and attenuation effects can be determined and removed from the refraction image and the absolute attenuation image to produce a nearly scatter-free image. Analyzer system 10 for a Laue system is basically the same as analyzer system 10 for a Bragg system, except that crystal analyzer 20 is a Laue type. As shown in FIG. 11, diffracted beam 22 passes through analyzer 20. The crystal of analyzer 20 preferably has the same material composition as the crystals of monochromator 12.

As shown in FIG. 11, an x-ray source is monochromated and collimated by double crystal monochromator 12. Depending upon the type of lattice planes for monochromator 12 and crystal analyzer 20, analyzer system 10 can have different sensitivity to refraction effects and rejection of scatter.

As shown in FIG. 11, x-ray beam 14 is monitored by ionization chamber 34 in order to maintain alignment of the double crystals of monochromator 12. Shutter 38 can be used to begin and end exposure. Ionization chamber 40 is preferably used to monitor a dose which is delivered to object 16. Absorber 36 can be used in combination with a scanning stage in order to set a skin entry dose which is delivered to object 16. As will be appreciated by one skilled in the art, such elements can also be included with a Bragg type crystal analyzer system such as shown in FIG. 1.

As the Laue type crystal analyzer 20 results in two different diffracted beams, the rocking curve for a Laue type crystal analyzer 20 includes two curves. A first curve represents points for diffracted beam 22 and a second curve represents points for forward diffracted beam 24.

When imaging at relatively high x-ray energies, reflection widths become relatively narrow and it can be difficult to physically maintain alignment of monochromator 12 and/or crystal analyzer 20. Some horizontal banding in the images can be caused by misalignment. In one preferred embodiment according to this invention, analyzer system 10 may comprise a feedback system to maintain such alignment by varying the angular position of monochromator 12 and/or crystal analyzer 30.

The method according to this invention can resolve refraction at any energy and thus will allow imaging at relatively higher x-ray energy levels. Thus a dose delivered to object 16 can be reduced while maintaining the same intensity to the detector.

The method of this invention can provide images in two dimensions, i.e., images that represent projections through an object, such as shown in FIGS. 5–9. In conventional radiography or mammography, the two-dimensional images are a type of shadow. In the method of this invention the images are not mere shadows, but an image formed from mathematical computations of parameters measured from the object.

As will be appreciated by one skilled in the art, the imaging methods disclosed herein, like conventional planar x-ray imaging, can be used to create computed tomographic images, including images of an object in three dimensions.

Computed tomographic imaging produces images that describe an object property at each point within a volumetric representation of the object. Computed tomographic images are usually displayed as slices. The imaging methods of this invention compute images for many views through an object, which can be used with existing integrals, such as by ordinary filtered back projection, to compute computed tomographic images.

The estimated angular intensity spectrum can be summarized by parameters defined specifically to highlight image features that are indicative of specific diseases. The analysis of the images provided by the methods of this invention can also be used to classify pixels into different categories of tissues or materials based on known parameters of various tissues or materials such as, for example, by obtaining supervised or unsupervised classification using statistical pattern recognition. Pixels can also be classified into different categories by a ratio value of the measured parameter values of a material, such as a ratio of the attenuation parameter to the refraction parameter or the ratio of the scatter parameter to the refraction parameter.

The methods of this invention thus provide improved x-ray imaging on a pixel-by-pixel basis of an object. The imaging methods of this invention can provide clearer, more defined images thereby allowing imaging of objects not typically detectable by conventional radiography, such as early stages of cancer growth, or thicker materials, such as cartilage.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A method for detecting an image of an object using at least one x-ray beam, the method comprising:

transmitting the at least one x-ray beam through a first view of the object and emitting from the object at least one transmitted beam;

directing the at least one transmitted beam at an analyzer;

positioning the analyzer at more than two angular positions and measuring an intensity of each said transmitted beam at each of the angular positions;

obtaining from the intensity measurements at the more than two angular positions at least one parameter of a measured angular intensity spectrum selected from a group consisting of a total intensity of the measured angular intensity spectrum, an angular divergence of the measured angular intensity spectrum, and a midpoint of the measured angular intensity spectrum;

obtaining at least one parameter of the object from at least one of the at least one parameter of the measured angular intensity spectrum; and using the at least one parameter of the object to display the image of the object.

2. The method according to claim 1, wherein the at least one parameter of the object includes at least one of an attenuation property, a refraction property and a scatter property of the object.

3. The method according to claim 1, further comprising preparing the at least one x-ray beam by diffraction from a monochromator.

4. The method according to claim 1, wherein the object is moved with respect to the analyzer and the image of the object is displayed at a plurality of second views of the object.

5. The method according to claim 1, wherein the analyzer includes a cyrstal.

6. The method according to claim 1, wherein each said parameter is displayed as one of a monochrome image and a pseudocolor image.

7. The method according to claim 1, wherein the image is displayed in one of two dimensions or three dimensions.

8. The method according to claim 1, wherein the image is displayed as a computed tomographic image.

9. The method according to claim 1, wherein the angular divergence of the measured angular intensity spectrum comprises a second central moment of the measured angular intensity spectrum.

10. The method according to claim 1, wherein the midpoint of the measured angular intensity spectrum comprises a centroid of the measured angular intensity spectrum.

11. A method for detecting an image of an object using at least one x-ray beam, the method comprising:

transmitting the at least one x-ray beam through a first view of the object and emitting from the object at least one transmitted beam;

directing the at least one transmitted beam at an analyzer;

positioning the analyzer at more than two angular positions and measuring an intensity of each said transmitted beam at each of the angular positions;

obtaining at least one parameter of a measured angular intensity spectrum from the intensity measurements at the more than two angular positions;

obtaining at least one parameter of a rocking curve of an analyzer system;

subtracting the parameter of the rocking curve from the parameter of the measured intensity spectrum to obtain a parameter of the object; and using the parameter of the object to display the image of the object.

12. A method for detecting an image of an object using at least one x-ray beam, the method comprising:

transmitting the at least one x-ray beam through a first view of the object and emitting from the object at least one transmitted beam;

directing the at least one transmitted beam at an analyzer;

positioning the analyzer at more than two angular positions and measuring an intensity of each said transmitted beam at each of the angular positions;

determining an estimated angular intensity spectrum from the intensity measurements at the more than two angular positions as a function of a sensitivity of an analyzer system;

obtaining at least one parameter of the object from the estimated angular intensity spectrum; and using the at least one parameter to display the image of the object.

13. The method according to claim 12, wherein the sensitivity of the analyzer is a rocking curve of the analyzer system.

14. The method according to claim 13, wherein a convolution integral is derived between the true angular intensity spectrum and the rocking curve.

15. The method according to claim 14, wherein a deconvolution operation inverts an effect of the convolution integral.

16. The method according to claim 15, wherein the estimated angular intensity spectrum is determined by numerically computing the deconvolution operation.

17. The method according to claim 16, wherein the at least one parameter includes at least one of an attenuation property, a refraction property and a scatter property of the object.

18. The method according to claim 15, wherein an estimated angular intensity spectrum is determined indirectly by postulating a model of the measured angular intensity spectrum a priori and by estimating the at least one parameter of the model.

19. A method for detecting an image of an object using at least one x-ray beam, the method comprising:
   transmitting the at least one x-ray beam through a first view of the object and emitting from the object at least one transmitted beam;
   directing the at least one transmitted beam at an analyzer;
   positioning the analyzer at more than two angular positions and measuring an intensity of each said transmitted beam at each of the angular positions, wherein one of the angular positions is at a peak of the rocking curve of an analyzer system;
   determining an attenuation parameter from at least two of the other more than two intensity measurements; and
   subtracting the attenuation parameter from the intensity measurement measured at the rocking curve peak to obtain a scatter parameter of the object; and
   using the scatter parameter to display the image of the object.

20. A method for detecting an image of an object using at least one x-ray beam, the method comprising:
   transmitting the at least one x-ray beam through a first view of the object and emitting from the object at least one transmitted beam;
   directing the at least one transmitted beam at an analyzer;
   positioning the analyzer at more than two angular positions and measuring an intensity of each said transmitted beam at each of the angular positions;
   obtaining more than one parameter from the intensity measurements at the more than two angular positions; and
   classifying all or part of the object into different categories of tissues or materials based on the obtained parameters.

21. The method of claim 20, further comprising classifying the tissue or material of the object by statistical pattern recognition of the obtained parameters.

22. The method according to claim 20, further comprising calculating a ratio value of at least two of the parameters and classifying the tissue or material of the object by the ratio value.

* * * * *